United States Patent
Walker et al.

(10) Patent No.: US 10,420,702 B2
(45) Date of Patent: ***Sep. 24, 2019

(54) CPR QUALITY ASSESSMENT ACCOUNTING FOR PAUSE ASPECT

(71) Applicant: Physio-Control, Inc., Redmond, WA (US)

(72) Inventors: Robert G. Walker, Seattle, WA (US); Ronald E. Stickney, Edmonds, WA (US); Fred W. Chapman, Newcastle, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 168 days.

This patent is subject to a terminal disclaimer.

(21) Appl. No.: 14/183,367

(22) Filed: Feb. 18, 2014

(65) Prior Publication Data

US 2014/0236053 A1    Aug. 21, 2014

Related U.S. Application Data

(63) Continuation-in-part of application No. 14/069,112, filed on Oct. 31, 2013.

(Continued)

(51) Int. Cl.
*G06Q 50/00* (2012.01)
*A61H 31/00* (2006.01)
(Continued)

(52) U.S. Cl.
CPC ........... *A61H 31/005* (2013.01); *A61B 5/024* (2013.01); *A61H 31/00* (2013.01); *A61H 31/007* (2013.01);
(Continued)

(58) Field of Classification Search
CPC ........ G06Q 50/22; G06Q 50/24; G06Q 40/08; G06Q 10/10; G06F 19/322; G06F 17/30;
(Continued)

(56) References Cited

U.S. PATENT DOCUMENTS

| 4,060,079 A | 11/1977 | Reinhold |
| 4,237,872 A | 12/1980 | Harrigan |

(Continued)

FOREIGN PATENT DOCUMENTS

| EP | 1057451 A2 | 12/2000 |
| EP | 1859770 A1 | 11/2007 |

(Continued)

OTHER PUBLICATIONS

Walker R, Brouwer T, Chapman F, Koster R. Lack of correlation between chest compression fractions over 0.4 and survival. Prehospital Emergency Care 2013; 17(1):118,A62. Abstract.

(Continued)

*Primary Examiner* — Tran N Nguyen
(74) *Attorney, Agent, or Firm* — Lane Powell PC

(57) ABSTRACT

Devices, systems, software and methods for CPR quality assessment. Patient data is received, derived from a session of administering sets of CPR chest compressions to a patient. The sets can be separated by pauses. In some embodiments, a penalty value can be determined for at least one of the pauses, from at least one control factor unrelated to a constant linear dependence on the pause duration. An indicative value can be derived from the penalty value. In some embodiments, at least some of the pauses are classified in one or more pause groups, depending on how well they meet one or more classification criteria. The indicative value can be derived for one of the pause groups. The indicative value can be output, and/or an alarm can be emitted if it (Continued)

CPR CHEST COMPRESSIONS SCENE exceeds a threshold. CPR quality assessment can be improved in real time, and provide feedback for training.

13 Claims, 10 Drawing Sheets

Related U.S. Application Data

(60) Provisional application No. 61/766,948, filed on Feb. 20, 2013.

(51) Int. Cl.
    *A61B 5/024*     (2006.01)
    *C07D 413/14*     (2006.01)
    *G06F 19/00*     (2018.01)
    *A61N 1/39*     (2006.01)
    *G06Q 10/00*     (2012.01)

(52) U.S. Cl.
    CPC .......... *A61N 1/3925* (2013.01); *C07D 413/14* (2013.01); *G06F 19/3481* (2013.01)

(58) Field of Classification Search
    CPC ........ G06F 19/30; G06F 19/32; G06F 19/321; G06F 19/324; G06F 19/325; G06F 19/326; G06F 19/328; G06F 19/34; G06F 19/3418; G06F 19/3456; G06F 19/346; G06F 19/3468; G06F 19/3475; G06F 19/3481; G06F 19/36; A61N 1/08; G16H 10/20; G16H 10/40; G16H 10/60; G16H 10/65; G16H 15/00; G16H 20/00; G16H 20/10; G16H 20/113; G16H 20/17; G16H 20/30; G16H 20/40; G16H 20/60; G16H 20/70; G16H 20/90; G16H 30/00; G16H 30/20; G16H 30/40; G16H 40/00; G16H 40/20; G16H 40/40; G16H 40/60; G16H 40/63; G16H 40/67; G16H 50/00; G16H 50/20; G16H 50/30; G16H 50/50; G16H 50/70; G16H 50/80; G16H 70/00; G16H 70/20; G16H 70/40; G16H 70/60; G16H 80/00

See application file for complete search history.

(56) References Cited

U.S. PATENT DOCUMENTS

| | | | |
|---|---|---|---|
| 4,397,306 A | 8/1983 | Weisfeldt et al. | |
| 4,424,806 A | 1/1984 | Newman et al. | |
| 4,570,615 A | 2/1986 | Barkalow | |
| 4,610,254 A | 9/1986 | Morgan et al. | |
| 4,797,104 A | 1/1989 | Laerdal et al. | |
| 4,928,674 A | 5/1990 | Halperin et al. | |
| 5,020,516 A | 6/1991 | Biondi et al. | |
| 5,077,667 A | 12/1991 | Brown et al. | |
| 5,261,394 A | 11/1993 | Mulligan et al. | |
| 5,334,070 A | 8/1994 | Yu et al. | |
| 5,490,820 A | 2/1996 | Schack et al. | |
| 5,716,318 A | 2/1998 | Manning | |
| 5,722,613 A | 3/1998 | Michael | |
| 5,743,864 A | 4/1998 | Baldwin, II | |
| 5,749,902 A | 5/1998 | Olson et al. | |
| 5,997,488 A | 12/1999 | Gelfand et al. | |
| 6,125,299 A | 9/2000 | Groenke et al. | |
| 6,334,070 B1 | 12/2001 | Nova et al. | |
| 6,351,671 B1 | 2/2002 | Myklebust et al. | |
| 6,356,785 B1 | 3/2002 | Snyder et al. | |
| 6,390,996 B1 | 5/2002 | Halperin et al. | |
| 6,398,745 B1 | 6/2002 | Sherman et al. | |
| 6,438,419 B1 | 8/2002 | Callaway et al. | |
| 6,676,613 B2 | 1/2004 | Cantrell et al. | |
| 6,697,671 B1 | 2/2004 | Myklebust et al. | |
| 6,827,695 B2 | 12/2004 | Palazzolo et al. | |
| 7,272,441 B1 | 9/2007 | Chapman et al. | |
| 7,311,680 B2 | 12/2007 | Lenhart et al. | |
| 7,630,762 B2 | 12/2009 | Sullivan et al. | |
| 7,717,855 B2 | 5/2010 | Caldarone et al. | |
| 7,805,191 B2 | 9/2010 | Walker et al. | |
| 8,060,199 B2 | 11/2011 | Walker et al. | |
| 8,135,460 B2 | 3/2012 | Sullivan et al. | |
| 8,343,081 B2 | 1/2013 | Walker | |
| 8,433,407 B2 | 4/2013 | Chapman et al. | |
| 8,795,208 B2 | 8/2014 | Walker | |
| 8,942,800 B2 | 1/2015 | Thiagrajan et al. | |
| 9,126,055 B2 | 9/2015 | Abdeen et al. | |
| 2002/0117173 A1 | 8/2002 | Lynn et al. | |
| 2002/0133197 A1 | 9/2002 | Snyder et al. | |
| 2003/0135085 A1 | 7/2003 | Bassuk et al. | |
| 2003/0135139 A1 | 7/2003 | Bassuk et al. | |
| 2003/0195775 A1 | 10/2003 | Hampton et al. | |
| 2004/0082888 A1 | 4/2004 | Palazzolo et al. | |
| 2004/0225238 A1 | 11/2004 | Sherman et al. | |
| 2004/0230140 A1 | 11/2004 | Steen | |
| 2005/0165335 A1 | 7/2005 | Sherman et al. | |
| 2006/0017350 A1 | 1/2006 | Hanahara et al. | |
| 2006/0089574 A1 | 4/2006 | Paradis | |
| 2006/0111749 A1 | 5/2006 | Westenskow et al. | |
| 2006/0173500 A1 | 8/2006 | Walker et al. | |
| 2006/0173501 A1* | 8/2006 | Stickney ................ A61B 5/046 607/5 |
| 2007/0004992 A1 | 1/2007 | Van Brunt et al. | |
| 2008/0146974 A1 | 6/2008 | Lind et al. | |
| 2009/0270930 A1 | 10/2009 | Walker et al. | |
| 2010/0015280 A1 | 1/2010 | Walker et al. | |
| 2010/0016910 A1 | 1/2010 | Sullivan et al. | |
| 2010/0022904 A1 | 1/2010 | Centen et al. | |
| 2010/0152800 A1 | 6/2010 | Walker et al. | |
| 2011/0082510 A1 | 4/2011 | Sullivan | |
| 2011/0297147 A1 | 12/2011 | Lick et al. | |
| 2012/0010543 A1* | 1/2012 | Johnson ................ A61N 1/3993 601/41 |
| 2012/0123224 A1 | 5/2012 | Packer et al. | |
| 2012/0136286 A1 | 5/2012 | Nova et al. | |
| 2013/0023781 A1 | 1/2013 | Freeman et al. | |
| 2013/0282069 A1* | 10/2013 | Thiagarajan ......... A61N 1/3993 607/3 |

FOREIGN PATENT DOCUMENTS

| | | |
|---|---|---|
| EP | 1933114 A1 | 6/2008 |
| GB | 2446124 A | 6/2008 |
| WO | 1999024114 A1 | 5/1999 |
| WO | 2004037154 A2 | 5/2004 |
| WO | 2007033050 A2 | 3/2007 |

OTHER PUBLICATIONS

Brouwer T, Walker R, Chapman F, Koster R. Duration of longest chest compression interruption predicts poor cardiac arrest survival independent of chest compression fraction. Circulation 2012;126:A87. Abstract.

International Search Report & Written Opinion by PCT Authority for PCT/US2014/017213, dated May 9, 2014.

Berg RA, et al., Part 5: adult basic life support: 2010 American Heart Association Guidelines for Cardiopulmonary Resuscitation and Emergency Cardiovascular Care. Circulation. Nov. 2, 2010;122(18 Suppl 3):S685-705.

Cave DM, et al., Part 7: CPR techniques and devices: 2010 American Heart Association Guidelines for Cardiopulmonary Resuscitation and Emergency Cardiovascular Care. Circulation. Nov. 2, 2010;122(18 Suppl 3):S720-8.

Chapman, F.W. et al., "A Feedback Controller for Ventilatory Therapy", Annals of Biomedical Engineering, 1985, 13, 359-372.

Cobb, Leonard A., Changing Incidence of Out-of-Hospital Ventricular Fibrillation, 1980-2000, JAMA, Dec. 18, 2002, p. 3008-3013, vol. 288, No. 23.

Diaz, et al., "Modifying the first minute of reperfusion: potential for myocardial salvage", Cardiovascular Research 62, 2004 pq 4-6 Elsevier B.V.

(56) References Cited

OTHER PUBLICATIONS

Galagudza et al., "Ischemic postconditioning: brief ischemia during reperfusion converts persistent ventricular fibrillation into regular rhythm", European Journal of Cardiothoracic Surgery, 25, (2004) p. 1006-1010 Elsevier B.V.
Halkos et al., The Society of Thoracic Surgeons, 2004, p. 961-969, Elsevier Inc.
Hallstrom et al., "Cardiopulmonary Resuscitation by Chest Compression Alone or with Mouth-To-Mouth Ventilation", May 25, 2000, The New England Journal of Medicine, vol. 342, No. 21, pp. 1546-1553.
Heusch, "Postconditioning, Old Wine in a New Bottle?" Journal of the American College of Cardiology, 2004, vol. 44, No. 5, p. 1111-1112, Elsevier Inc.
International Search Report and Written Opinion, PCT/US2005/39633, Intl. filed Nov. 2, 2005, 4 pages.
Kern et al., "Efficacy of Chest Compression-Only BLS CPR in the Presence of an Occluded Airway", 1998, Elsevier Science Ireland Ltd., Resuscitation 39 (1998), Accepted Nov. 11, 1998, pp. 179-188.
Kin et al., "Postconditioning attenuates myocardial ischemia-reperfusion injury by inhibiting events in the early minutes of reperfusion", Cardiovascular Research 62, 2004, p. 75-85, Elsevier B.V.
Maquet Servo Ventilator 900 C/D/E, Service Manual, Maquet Critical Care AB, May 2009, 55 pages.
Neumar RW, et al.,Part 8: Adult advanced cardiovascular life support: 2010 American Heart Association Guidelines for Cardiopulmonary Resuscitation and Emergency Cardiovascular Care. Circulation. Nov. 2, 2010;122(18 Suppl 3): S729-67.
Ovize M, et al., "Working Group of Cellular Biology of Heart of European Society of Cardiology. Postconditioning and protection from reperfusion injury: where do we stand?" Position paper from the Working Group of Cellular Biology of the Heart of the European Society of Cardiology. Cardiovasc Res. Aug. 1, 2010;87(3):406-423.
Part 4: Adult Basic Life Support, Circulation, 2005, 112: IV-18 to IV-34.
Part 6: CPR Techniques and Devices, Circulation, 2005, 112: IV-47 to IV-50.
Responsive Amendment dated Jul. 1, 2009 for U.S. Appl. No. 11/961,687 (13 pgs.).
Segal N, et al., "Ischemic postconditioning at the initiation of cardiopulmonary resuscitation facilitates functional cardiac and cerebral recovery after prolonged untreated ventricular fibrillation", Resuscitation. Nov. 2012;83(11):1397-1403.
Travers AH, et al., Part 4: CPR overview: 2010 American Heart Association Guidelines for Cardiopulmonary Resuscitation and Emergency Cardiovascular Care. Circulation. Nov. 2, 2010;122(18 Suppl 3):5676-5684.
Tsang et al., "Postconditioning: A Form of Modified Reperfusion Protects the Myocardium by Activating the Phosphatidylinositol 3-Kinase-Akt Pathway", Circulation Research, 2004 p. 230-232 American Heart Association Inc.
U.S. Appl. No. 11/272,177, filed Nov. 10, 2005, CPR Performance Reporting Systems.
Wang JY, et al., "Ischemic postconditioning protects against global cerebral ischemia/reperfusion-induced injury in rats", Stroke. Mar. 2008;39(3):983-990.
Weisfeldt, Resuscitation After Cardiac Arrest, JAMA, Dec. 18, 2002, p. 3035-3038, vol. 288, No. 23.
Wik, Lars, Delaying Defibrillation to Give Basic Cardiopulmonary Resuscitation to Patients With Out-of-Hospital Ventricular Fibrillation, JAMA, Mar. 19, 2003, p. 1389-1395, vol. 289, No. 11.
Wik, Lars, MD, PhD, Quality of Cardiopulmonary Resuscitation During Out-of Hospital Cardiac Arrest, (Reprinted) JAMA, Jan. 19, 2005—vol. 293, No. 3, pp. 299-304.
Yang et al., "Multiple, Brief Coronary Occlusions During Early Reperfusion Protect Rabbit Hearts by Targeting Cell Signaling Pathways", Journal of the American College of Cardiology, 2004 vol. 44 No. 5 PO 1103-1110 Elsevier Inc.
Yannopoulos D, et al., "Controlled pauses at the initiation of sodium nitroprusside-enhanced cardiopulmonary resuscitation facilitate neurological and cardiac recovery after 15 mins of untreated ventricular fibrillation", Crit Care Med. May 2012;40(5):1562-1569.
Yannopoulos D, et al., "Ischemic post-conditioning and vasodilator therapy during standard cardiopulmonary resuscitation to reduce cardiac and brain injury after prolonged untreated ventricular fibrillation", Resuscitation. Aug. 2013;84(8)1143-9. Epub Jan. 29, 2013.
Zhao, et al., "Inhibition of myocardial injury by ischemic postconditioning during reperfusion: comparison with ischemic preconditioning", Am J Physiol Heart Circ Physiol 285, 2003, p. H579-H588 The American Physiological Society.
Zhao, Heng, "The Protective Effects of Ischemic Postconditioning against Stroke: From Rapid to Delayed and Remote Postconditioning", The Open Drug Discovery Journal, 2010, 2, 138-147.
Zhou Y, et al., "Postconditioning in cardiopulmonary resuscitation: a better protocol for cardiopulmonary resuscitation", Med Hypotheses. Sep. 2009;73(3):321-323. 2009.03.014. Epub Apr. 24, 2009.
Zoll Data Systems, "RescueNet Code Review, Getting Started Guide—Version 5.20", dated Aug. 25, 2005.
International Preliminary Report on Patentability dated Aug. 25, 2015, by PCT Authority for PCT/US2014/017213 International filing date Feb. 19, 2014.

* cited by examiner

CPR CHEST COMPRESSIONS SCENE

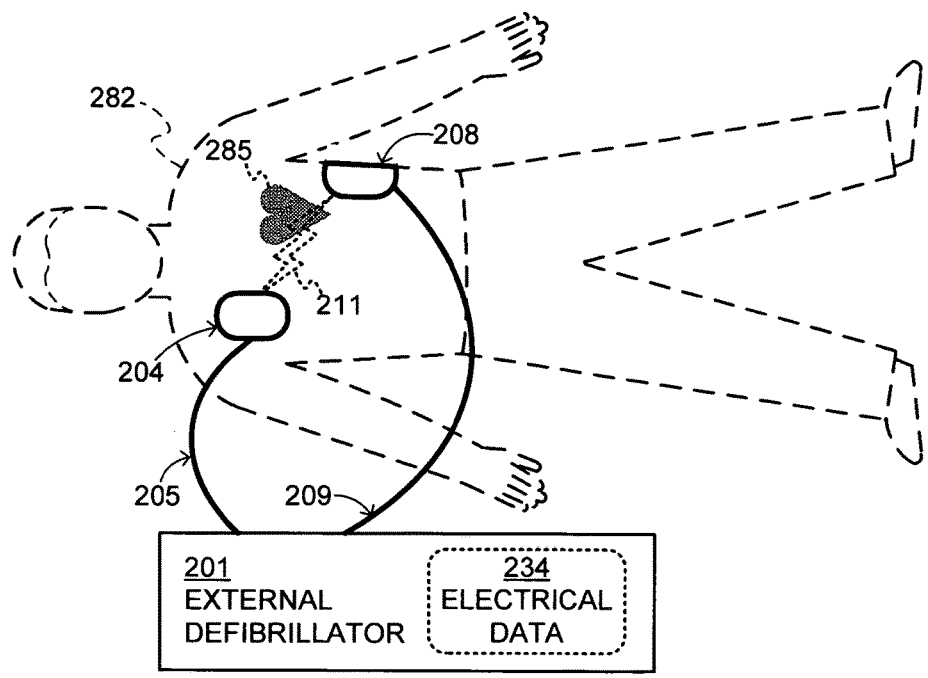
FIG. 2   *DEFIBRILLATION SCENE*
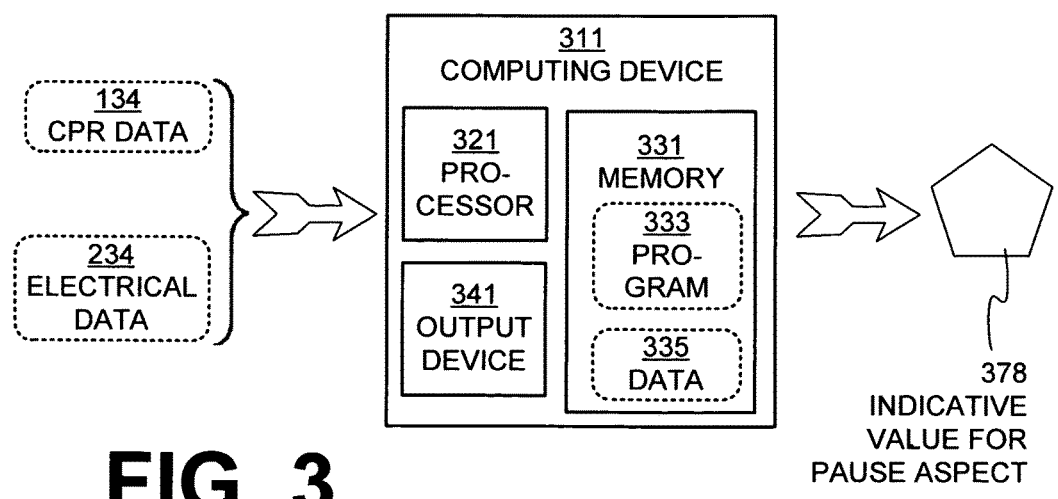
FIG. 3

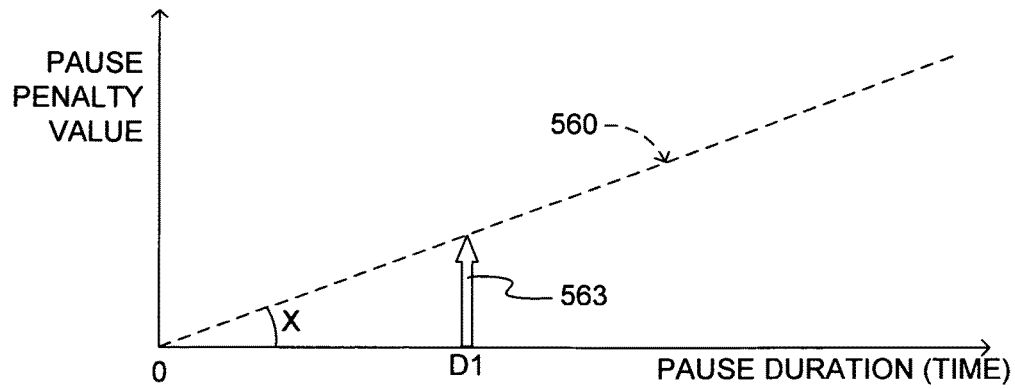
DETERMINING PAUSE PENALTY VALUES
FIG. 5 (PRIOR ART)
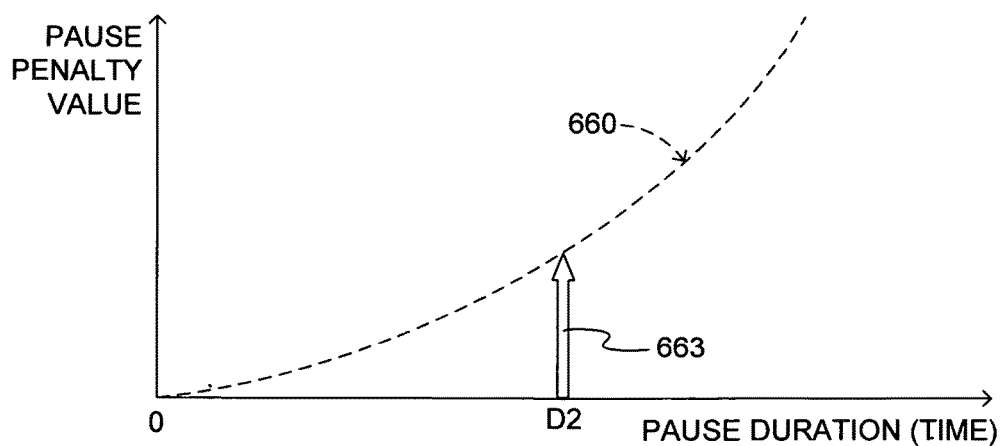
FIG. 6  DETERMINATION OF PAUSE PENALTY VALUES

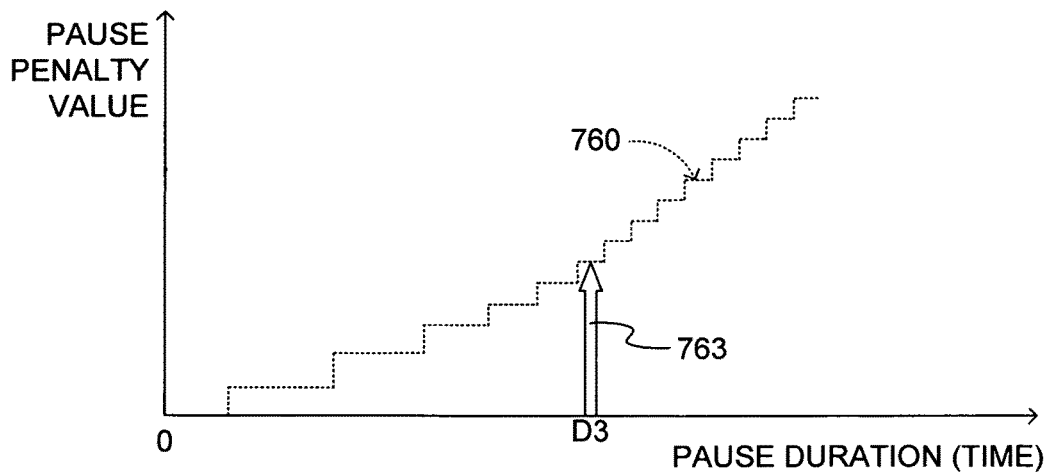
FIG. 7  *DETERMINATION OF PAUSE PENALTY VALUES*
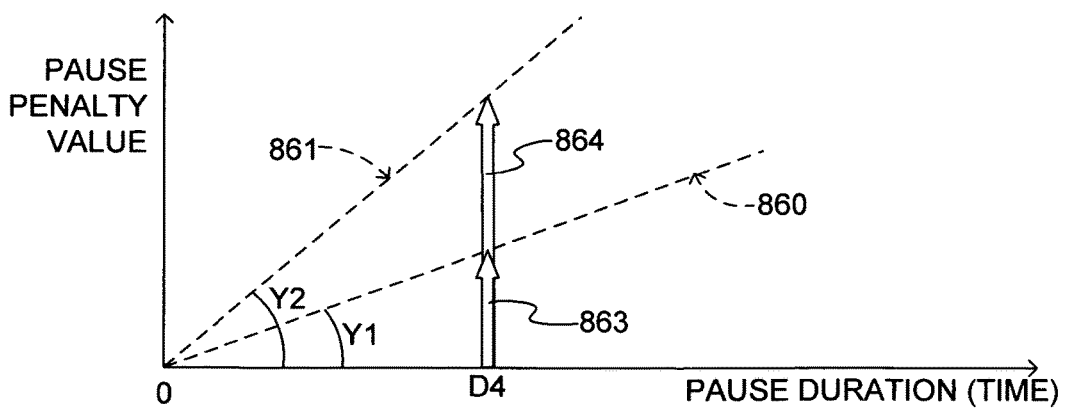
FIG. 8  *DETERMINATION OF PAUSE PENALTY VALUES*

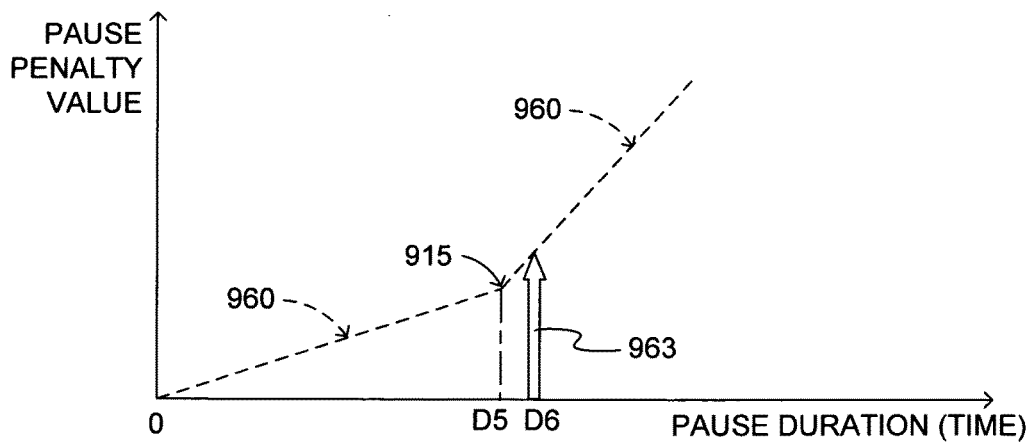
FIG. 9  *DETERMINATION OF PAUSE PENALTY VALUES*
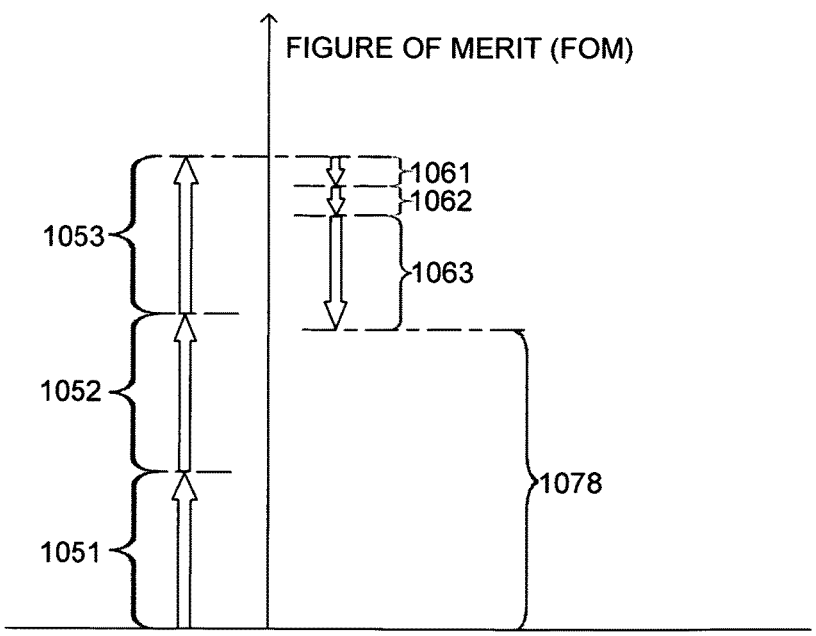
FIG. 10  *COMPUTING FIGURE OF MERIT (FOM)*

CLASSIFYING PAUSES
IN CPR CHEST COMPRESSIONS
(ANY CRITERION)

INDICATIVE VALUES
(BAR CHART FORMAT)

INDICATIVE VALUES
(PIE CHART FORMAT)

CPR QUALITY ASSESSMENT ACCOUNTING FOR PAUSE ASPECT

CROSS REFERENCE TO RELATED PATENT APPLICATIONS

This patent application claims priority from U.S. Provisional Patent Application Ser. No. 61/766,948, filed on Feb. 20, 2013, titled: "PAUSE DURATION DISTRIBUTION INDICATOR FOR A CPR QUALITY REPORT", the disclosure of which is hereby incorporated by reference for all purposes.

This patent application is a Continuation-in-Part of copending U.S. patent application Ser. No. 14/161,269, filed on Jan. 22, 2014, all commonly assigned herewith.

BACKGROUND

In humans, the heart beats to sustain life. In normal operation, the heart pumps blood through the various parts of the body. Sometimes the heart malfunctions, in which case it can beat irregularly, or not at all. The cardiac rhythm is then generally called an arrhythmia. Some types of arrhythmia may result in inadequate blood flow, thus reducing the amount of blood pumped to the various parts of the body. Some arrhythmias may even result in a Sudden Cardiac Arrest (SCA). In a SCA, the heart fails to pump blood effectively and, if not treated, death can occur. In fact, the American Heart Association (AHA) reported in 2014 that SCA results in more than 500,000 deaths per year in the United States alone. Further, a SCA may result from a condition other than an arrhythmia. One type of arrhythmia associated with SCA is known as Ventricular Fibrillation (VF). VF is a type of heart malfunction where the ventricles make rapid, uncoordinated movements, instead of the normal contractions. When that happens, the heart does not pump enough blood to deliver enough oxygen to the vital organs. The person's condition will deteriorate rapidly and, if not reversed in time, they will die soon, e.g. within ten minutes.

Ventricular Fibrillation can often be reversed using a life-saving device called a defibrillator. A defibrillator, if applied properly, can administer an electrical shock to the heart. The shock may terminate the VF, thus giving the heart the opportunity to resume pumping blood. If VF is not terminated, the shock may be repeated, often at escalating energies.

A challenge with defibrillation is that the electrical shock must be administered very soon after the onset of VF. There is not much time: the survival rate of persons suffering from VF decreases by about 10% for each minute the administration of a defibrillation shock is delayed. After about 10 minutes, the rate of survival for SCA victims averages less than 2%.

During VF, the person's condition deteriorates, because blood is not flowing to the brain, heart, lungs, and other organs. Blood flow must be restored, if resuscitation attempts are to be successful.

Cardiopulmonary Resuscitation (CPR) is one method of forcing blood flow in a person experiencing cardiac arrest. In addition, CPR is the primary recommended treatment for some patients with some kinds of non-VF cardiac arrest, such as asystole and Pulseless Electrical Activity (PEA). CPR is a combination of techniques that include chest compressions to force blood circulation, and rescue breathing to force respiration.

Properly administered CPR provides oxygenated blood to critical organs of a person in cardiac arrest, thereby minimizing the deterioration that would otherwise occur. As such, CPR can be beneficial for persons experiencing VF, because it slows the deterioration that would otherwise occur while a defibrillator is being retrieved. Indeed, for patients with an extended down-time, survival rates are higher if CPR is administered prior to defibrillation.

CPR chest compressions must be administered continuously, or nearly so. Methods have been devised for assessing a rescue team's performance, so as to help them improve their training. A method by Physio-Control, Inc. is described in U.S. Pat. No. 8,080,199 B2, which is hereby incorporated by reference. One or more figures of merit are computed about the administered CPR. Figures of merit can be metrics.

A specific metric that has received much focus and emphasis is the chest compression fraction, which is also known as "hands-on time", chest compression ratio, CPR ratio, flow time, etc. The chest compression fraction represents a ratio of the total amount of time that chest compressions were performed during an interval of interest, up to and including an entire resuscitation, over the total duration of that interval of interest.

The chest compression fraction is attractive because it distills what is thought to be a dominant aspect of CPR quality down to a simple interpretable number. That aspect is the answer to "for how much time were chest compressions actually being done while the patient needed them?" While that is true, a problem remains that interruptions in the chest compressions are not properly accounted for.

BRIEF SUMMARY

The present description gives instances of devices, systems, software and methods for CPR quality assessment, which account for one or more aspects of pauses in the CPR chest compressions. The use of such devices, systems, software and methods may help overcome problems and limitations of the prior art.

Patient data can be received. The patent data may be derived from a session of administering sets of CPR chest compressions to a patient. The sets can be separated by pauses.

In some embodiments, a penalty value can be determined for at least a certain one of the pauses. The penalty value can be determined from at least one control factor unrelated to a constant linear dependence on a duration of the certain pause. An indicative value can be derived from the penalty value.

In some embodiments, at least some of the pauses are classified in one or more pause groups, depending on how well they meet one or more classification criteria. The indicative value can be derived for one of the pause groups.

In many embodiments, the indicative value can be output for the benefit of the user. In many embodiments, an alarm can be emitted if the indicative value exceeds a threshold, so that a rescuer will be alerted to resume compressions.

An advantage over the prior art is that pauses in the CPR chest compressions can be accounted for in better correspondence with how harmful they could be to the patient. As such, a better CPR quality assessment can be achieved in real time. Also, post event analysis review can provide useful feedback to rescuers for improved performance the next time.

These and other features and advantages of this description will become more readily apparent/from the following Detailed Description, which proceeds with reference to the drawings, in which:

BRIEF DESCRIPTION OF THE DRAWINGS

FIG. 2 is a diagram of a scene where a defibrillator is applied to the chest of a patient, and is storing patient electrical data according to embodiments.

FIG. 3 is a diagram of a computing device configured according to embodiments.

FIG. 5 is a diagram showing how penalty values for pauses can be determined in the prior art.

FIG. 6 is a diagram showing how a pause penalty value is computed according to an embodiment.

FIG. 7 is a diagram showing how a pause penalty value is computed according to another embodiment.

FIG. 8 is a diagram showing how a pause penalty value is computed according to an additional embodiment.

FIG. 9 is a diagram showing how a pause penalty value is computed according to a further embodiment.

FIG. 10 is a diagram illustrating graphically components for deriving a figure of merit (FOM) from some of the data of FIG. 4 according to embodiments.

DETAILED DESCRIPTION

As has been mentioned, the present description is about devices, systems, software and methods for CPR quality assessment, which account for one or more aspects of pauses in the CPR chest compressions. Embodiments are now described in more detail.

Figure 1:
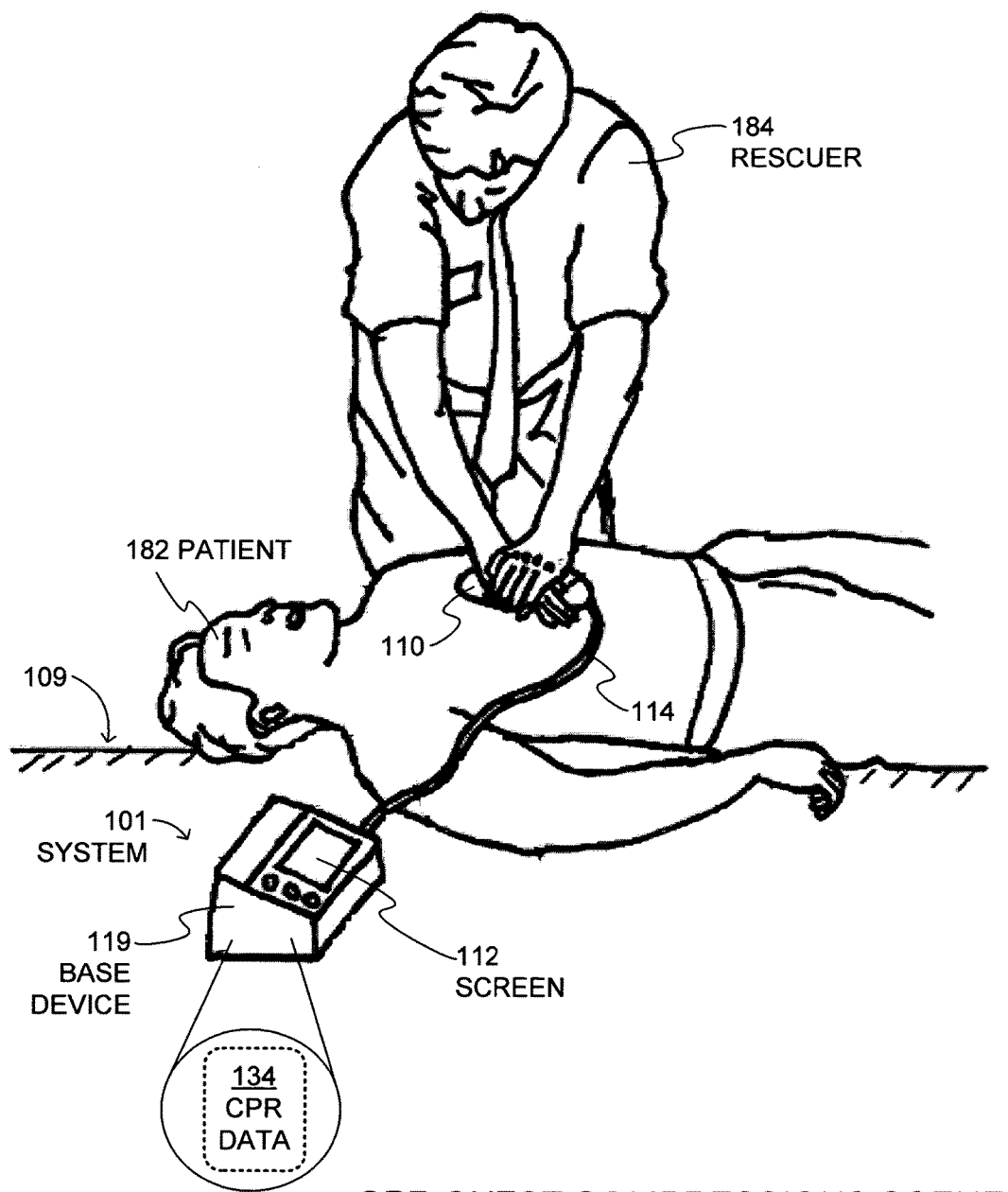
FIG. 1 is a diagram of a scene where a rescuer is performing chest compressions on a patient using a CPR feedback apparatus according to embodiments.

FIG. 1 is a diagram of a scene where a rescuer 184 is performing chest compressions on a patient 182 who is lying on ground 109. Rescuer 184 is also using a sample system 101, which is made according to embodiments. Particular system 101 is for real time CPR feedback, but that need not be the case according to embodiments—it might have other uses in addition or in lieu of CPR feedback.

System 101 includes a sensor that is configured to detect sets of CPR chest compressions received by patient 182. The sets of CPR chest compressions can be separated by pauses. The sensor can be made in any way known in the art for CPR feedback devices, including the types that are placed on the chest or not. For example, a sensor could be a video camera that is capturing the event. The video of the scene could be analyzed afterwards to see when CPR compressions and pauses occurred. The sensor can include the types that just sense that chest compressions are being performed, without particularly sensing displacement, velocity or acceleration. For the example of FIG. 1 only, the sensor is implemented by sensor 110, which is configured to be placed on the patient's chest, and detect a time profile of a displacement of the chest of patient 182. The sensor could be somewhere else on the body, such as be an airway flow sensor, or a sensor on the abdomen, which could also work to tell when the chest is pushed on. A sensor under the body could also be used to identify compressions. A sensor on the rescuer's hand or device that pushes on the chest could suffice, too.

System 101 also includes a base device 119. Base device 119 may be operatively coupled with the sensor. In the example of FIG. 1, coupling is by wire 114, although coupling may be wireless, such as magnetic, electromagnetic, and so on. Base device 119 may generate patient data from the sets of CPR chest compressions detected by the sensor. The generated patient data is shown in the example of FIG. 1 as CPR data 134 within base device 119. Of course, this CPR data reflects the above-mentioned sets of CPR chest compressions that are separated by pauses.

Base device 119 has a user interface. User interface may be implemented in any way known in the art for being used by rescuer 184. The user interface will be used in connection with the data. In the example of FIG. 1, the user interface includes at least a screen 112, which can display metrics of computed statistics, explanations and other guidance. The user interface can be configured to emit an alarm, such as an audible signal. Such aspects to be communicated can be combined. For example, there could be auditory or graphic representation that indicates penalty associated at a particular instant in a pause. Such a representation can be a growing red geometric shape on a screen, a light that blinks at an increasing rate, or a sound that increases in pitch or volume, where the increase is directly tied to the penalty that will be assessed for continuing to pause forward from that instant. The output of the user interface can become part of the patient record.

As mentioned above, the system need not be dedicated to being only a CPR feedback system, such as system 101. Rather, the system could be part of a monitor-defibrillator, in which case the base device has correspondingly additional capabilities. For example, the base device could include a defibrillation module, configured to defibrillate the patient, if need be.

System 101 further includes a processor, which is not shown in FIG. 1. It is preferred that the processor is within base device 119. The processor can be configured to derive an indicative value for the CPR chest compressions according to embodiments. More particularly, the processor may input patient data derived from a session of administering to a patient sets of CPR chest compressions that are separated by pauses. A penalty value for at least a certain one of the pauses can be determined. The determination can be made as described later in this document. The indicative value can be derived from the penalty value. Examples are described in more detail later in this document.

The user interface of the system can be configured to output the indicative value. In the example of FIG. 1, screen 112 of system 101 can display the value.

The user interface can be configured to output an alarm, if the indicative value exceeds a threshold. For example, the user interface can also include a speaker, a beeper, a light, and so on. The alarm would be superfluous, if it could be guaranteed that rescuer 184 will always be looking at screen 112. However, a reason for an unduly long pause may be that rescuer 184 has become distracted with other activities or circumstances of the rescue session, in which case he is not necessarily looking at screen 112, and therefore an audible alarm may be required in addition to what may be shown in screen 112. Preferably, the alarm can be turned off, either at the settings or by the user, especially because in some instances undetectable to system 101, pausing will be appropriate. For example, if the patient regains circulation and the machine cannot detect this, continuing an alarm would not be well tolerated by rescuers.

FIG. 2 is a diagram of a defibrillation scene. A patient 282 is lying on his back. Patient 282 could be a patient in a hospital, or a pre-hospital patient such as someone found unconscious. Patient 282 is experiencing a condition in their heart 285, which could be Ventricular Fibrillation (VF), Ventricular Tachycardia (VT), etc.

A portable external defibrillator 201 has been brought close to patient 282. Defibrillator 201 may incorporate system 101 of FIG. 1, or not. At least two defibrillation electrodes 204, 208 are usually provided with external defibrillator 201, and are sometimes called electrodes 204, 208. Electrodes 204, 208 are coupled with external defibrillator 201 via respective electrode leads 205, 209. A rescuer (not shown in FIG. 2) has attached electrodes 204, 208 to the skin of patient 282. Defibrillator 201 can administer, via electrodes 204, 208, a brief, strong electric pulse 211 through the body of patient 282. Pulse 211, also known as a defibrillation shock, goes also through heart 285, in an attempt to restart it, for saving the life of patient 282.

Defibrillator 201 can be one of different types, each with different sets of features and capabilities. It could be a monitor-defibrillator, because it is typically formed as a single unit in combination with a patient monitor. Or it could be an Automated External Defibrillator (AED).

Defibrillator 201 is capable of detecting electrical parameters of patient 282, and storing them as electrical data 234 of patient 282. Electrical data 234 may include ECG (electrocardiogram) data, or data about the impedance of the patient, as measured between electrodes 204, 208.

At least impedance data can be converted to data derived from a session of CPR chest compressions. This is possible because, when a patient's chest is compressed, their impedance may change, and the chest compression may cause motion artifact in the impedance data.

FIG. 3 is a diagram of a computing device 311 configured according to embodiments. Computing device 311 may be a general purpose computer, or a module within a host system such as system 101, or within an external defibrillator such as external defibrillator 201. Examples and details can be found in the incorporated U.S. Pat. No. 8,060,199 B2.

Computing device 311 includes a processor 321. Processor 321 is configured to input patient data that is derived from administering CPR chest compressions to a patient, for example in a single session. An example of such data is CPR data 134. Such data may be acquired directly, e.g. as described above, or derived from electrical data 234 as mentioned above. Processor 321 can be further configured to compute an indicative value 378 from the inputted patient data. Indicative value 378 can be for a pause aspect of the CPR chest compressions. It will be appreciated that indicative value 378 can be context sensitive.

Computing device 311 also includes one or more non-transitory storage media. Such media include but are not limited to volatile memory, non-volatile memory (NVM), read only memory (ROM); random access memory (RAM); magnetic disk storage media; optical storage media; smart cards, flash memory devices, etc. In the example of FIG. 3, the non-transitory storage medium is a memory 331. These storage media, individually or in combination with others, can have stored thereon data such as data 335. Data 335 can be the inputted patient data. Interim computation data, and so on. These storage media can have also stored thereon one or more programs, such as program 333. The programs can include instructions in the form of code, which processor 321 may be able to execute upon reading. Executing is performed by physical manipulations of physical quantities, and may result in the functions, processes, actions and/or methods to be performed, and/or the processor to cause other devices or components or blocks to perform such functions, processes, actions and/or methods.

Computing device 311 additionally includes an output device 341. Output device 341 may be an output port that communicates indicative value 378. The value thus communicated may be received and displayed by a screen, in post-event review analysis. Or, if computing device 311 is part of a system such as system 101, output device 341 can communicate indicative value 378, which can in turn communicate it to the rescuer via the user interface.

Embodiments of computations of indicative value 378 are now described in more detail. These computations are made relative to the patient data. An example is now described.

Figure 4:
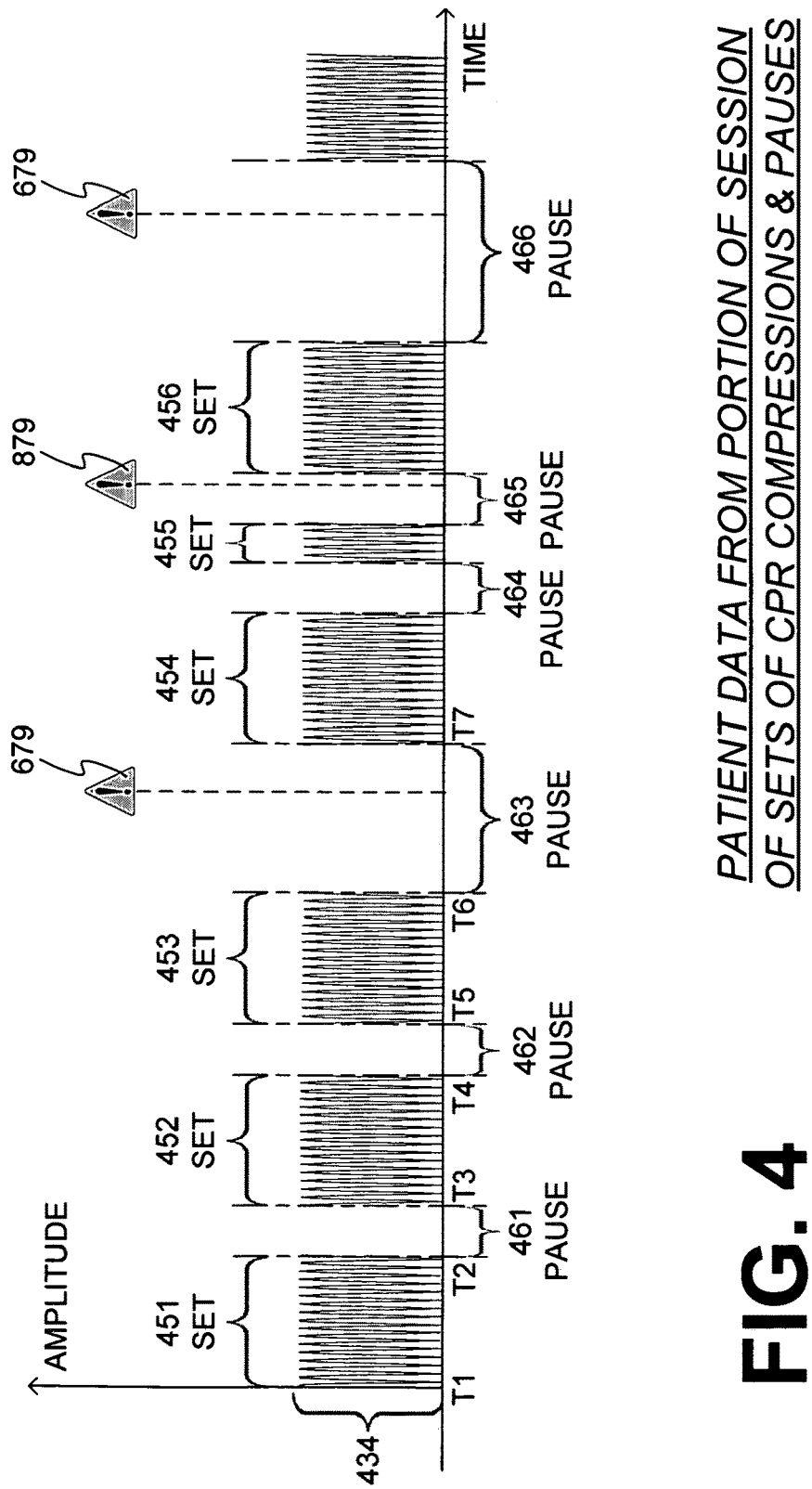
FIG. 4 is a time diagram of patient data, which are derived from a portion of a session of CPR chest compressions.

FIG. 4 is a time diagram of sample patient data 434, which can be derived from a portion of a session of CPR chest compressions. More particularly, data 434 is data of a time profile of a displacement of the patient's chest, as he is receiving CPR chest compressions. Since data 434 denotes compression depth, it can alternately be measured downward from zero, not upwards as in FIG. 4, but that does not make any difference for this description. Plus, data 434 are not from the entire session; rather, a convenient starting time T1 has been chosen on the time axis in this example only, while other starting times may be chosen, even before time T1.

Moreover, data 434 have been parsed into sets 451, 452, . . . 456 of CPR chest compressions. Within each of these sets there are compressions and releases of the patient chest that alternate rather quickly. It will be observed that the first few sets start and stop at times T1, T2, . . . , T7. More such times could be shown, but are not, so as to not clutter FIG. 4 unnecessarily. These times can be used to measure the duration of sets 451, 452, . . . , 456, and can be used in computations according to embodiments.

In addition, it will be observed that sets 451, 452, . . . , 456 are separated by pauses 461, 462, 463, 464, 465. Plus, a pause 466 follows set 456. These pauses take place when rescuer 184 might interrupt administering chest compressions, so as to administer ventilations or perform other activities of the rescue effort. For purposes of this document, the releases from the chest compressions that are within one of the sets are not considered to be pauses. The time durations of pauses 461, 462, . . . , 466 can also be measured on the time axis, and can be used in computations according to embodiments. FIG. 4 also shows emitted alarms 679, 879 during some of the pauses, which will be described later in this document.

In some embodiments, a patient record can be created from the patient data, to which other elements can be added, for example by being superimposed. An image of such a patient record could be the patient data of FIG. 4, to which alarms have been superimposed, as will be described later in this document. Other elements that can be superimposed are data about any one of the pauses, plus the values of penalties about the pauses. In some embodiments, a reviewer afterwards can click through the data of the pauses, to analyze them. Clicking can be through the pauses as they occurred in time, hierarchically based on their penalty values, or in another order.

It was mentioned above that embodiments may be practiced during the rescue session. Moreover, output device 341 or the user interface can be further configured to emit an alarm, if the indicative value exceeds a respective threshold.

It will be appreciated that embodiments may be practiced after the fact, in the context of a post-event review. In such cases, the indicative value can be computed using the patient data in its entirety, i.e. the patient data of the entire session. In such cases, the penalty value can be determined using the patient data in its entirety. Other embodiments may be practiced using only some of the patient data in the session. For example, the indicative value can be computed at least once during the rescue session, and shown to rescuer 184 using screen 112. In such cases, the penalty value can be determined at least once without using all the patient data of the session.

Determining the penalty values for pauses is now described in more detail. For reference, examples are first described where a penalty value for a pause is determined based on a constant linear dependence with a duration of the pause.

FIG. 5 is a diagram showing how penalty values for pauses can be determined in the prior art. In other words, it shows the computation of penalties due to pauses, such as pauses 461, 462, etc. In FIG. 5, the penalty value for a pause is plotted against a duration of the pause. The relationship is linear, denoted by a straight line 560. The relationship is also constant, as line 560 has a fixed slope. From trigonometry, the slope can be found from the tangent of angle X. For a duration D1, the penalty has the value of arrow 563, which starts from the horizontal time axis and reaches up to line 560. In other words, penalty 563 has a value determined from a constant linear dependence 560 on a duration D1 of its respective pause.

There are problems with the linear relationship of FIG. 5, because it does not capture the distribution of pauses. For example, while a single unduly long pause can have a harmful effect on a patient, its unduly long duration can be obscured, if it is added to and averaged with other short pauses. Second, not all pauses have the same effect of the patient. For example, some pauses that start after an unduly short set of CPR compressions are more harmful to the patient, even if they are not long. An example is the beginning of pause 465, after unduly short set 455.

According to embodiments, for at least a certain one of the pauses, determining can be performed from at least one control factor. That control factor can be unrelated to a constant linear dependence on a duration of the certain pause. In other words, in some embodiments, the penalty value is not merely a duration of the certain pause, as given by FIG. 5.

Examples of such control factor according to embodiments are now described. In addition, these individually described examples of control factors can be combined as desired. These examples are described in terms also of the certain penalty value shown on the vertical axis, while the pause duration is shown in the horizontal axis. They should be contrasted to the example of FIG. 5, which shows the pause penalty value as being determined from the constant linear dependence 560 on the duration of the pause.

FIG. 6 is a diagram showing how a pause penalty value is computed according to an embodiment. In this embodiment, the control factor includes a nonlinear relationship 660 of the certain penalty value with the pause duration, for at least a range of possible values of the duration. For example, at duration D2, the penalty value is represented by the length of arrow 663. Plus, in a range of values around D2, the certain penalty value changes nonlinearly with the duration.

An advantage of the non-linearly increasing penalty value is that unduly longer pauses can become penalized disproportionately, as desired. Plus, a nonlinear relationship such as relationship 660 might be responsible for causing an alarm 679 to be emitted. Alarm 679 is shown in FIG. 4, superimposed over the patient data, occurring during pauses 463, 466. Upon perceiving emitted alarm 679, rescuer 184 may reprioritize doing compressions.

Such embodiments should be tempered with the knowledge of other factors. For example, for a pause that includes delivery of a shock, no penalty at all might be applied. The rescuer might have stopped performing CPR compressions because they may have been instructed to stand clear. The duration for which penalty is determined can be reduced by 5 seconds in either direction of the shock delivery.

FIG. 7 is a diagram showing how a pause penalty value is computed according to another embodiment. In this embodiment, the control factor includes a staircase-type relationship 760 of the certain penalty value with the pause duration, for at least a range of possible values of the duration—here the entire shown range. For example, at duration D3, the penalty value is represented by the length of arrow 763. It will be recognized that the specific staircase-type relationship 760 also increases non-linearly at higher values, although that is not necessary for practicing the invention.

FIG. 8 is a diagram showing how a pause penalty value is computed according to an additional embodiment. In this embodiment, the control factor includes a relationship with different rates of increase of the certain penalty value with the duration, the rates being different depending on a condition. Two possible rates 860, 861 are shown. Rates 860, 861 are linear, but that is for example only. In fact, they could even have different shapes. Rate 860 has a slope given by the tangent of angle Y1, while rate 861 has a slope given by the tangent of angle Y2. Rate 861 is steeper, and accumulates penalty value faster. For example, at duration D4, if rate 860 is applied, the penalty value is represented by the length of arrow 863. However, if steeper rate 861 is applied, the penalty value is represented by the length of larger arrow 864. As such, the dependence is linear, but not constant.

Accordingly, the penalty value can be accumulated faster, depending on a condition. There can be any number of possible conditions.

In one embodiment, the condition may include the duration of a set of chest compressions prior to the pause; if that prior set is too short, then the pause cannot afford to be too long. For example, a portion where the relationship increases steeply, such as in relationship 861, might be responsible for causing an alarm 879 to be emitted. Alarm 879 is shown in FIG. 4, superimposed over the patient data, during pause 465. Pause 465 is not itself long, but takes place after an unduly short set 455. Upon perceiving emitted alarm 879, rescuer 184 may reprioritize doing compressions.

In another embodiment, the condition may include a ratio of a total duration of pauses to a total duration of chest compressions for a preceding time interval, such as the preceding three minutes, or the ventilation rate within the preceding interval of interest, such as 30 sec. In an additional embodiment, the condition may include proximity to the beginning of the recording, i.e. to the portion of the session that is known, or to an event of significance, such as defibrillation shock, beginning of mechanical CPR, user-identified time of collapse, and so on.

In one more embodiment, a present characterization can be input. The present characterization can be of a cardiac rhythm of the patient whose data is being used, in order to take into account how well the patient is doing. Then the condition may include the present characterization of the cardiac rhythm. For example, the penalty value can be accumulated at different speeds, depending on whether the characterization is "shockable", "bradycardia/PEA/asystole" or "ROSC-like", where "PEA" stands for Pulseless Electrical Activity, and "ROSC" stands for Return of Spontaneous Circulation.

FIG. 9 is a diagram showing how a pause penalty value is computed according to a further embodiment. For example, at duration D6, the penalty value is represented by the length of arrow 963. In this embodiment, relationship 960 has an inflection point 915 at a cross-over duration D5. The value of the penalty has a constant linear dependence on the duration for values of the duration up to cross-over duration D5, and also after, but at a different rate. As such, the dependence is linear, but not constant.

If a physiology model is computed, in whole or in part, then the above-described embodiments might be refined.

In a real time-display embodiment, the indicative value can further serve as a "pause tolerability index", reflecting how tolerant the patient's physiology is estimated to be to a reasonable-duration pause starting at that instant in time. In such an embodiment, the indicative value could be derived either by 1) using the entire recording, from the beginning of data until that point in time, equally weighted across that interval, or 2) weighting recent history more strongly, and/or only deriving the measurement from a recent time interval, such as the most recent 2 (or 5, etc.) minutes.

The indicative value may be derived in any number of ways. Examples are now described. In some embodiments, the indicative value indicates the penalty value, which may have been computed as above. In some embodiments, additional penalty values are computed for others of the pauses. Then the indicative value can be derived also from the additional penalty values.

In some embodiments, the indicative value is a Figure Of Merit (FOM) for at least some of the sets of CPR chest compressions. The FOM may have been derived also from the penalty value and the additional penalty values. In embodiments, all pauses contribute respective penalties to the FOM, and that each of the penalties has a value determined consistently with the value of the certain penalty. In some of those embodiments, all penalties are computed the same way. It is customary to express a Figure Of Merit as a positive number, in which case the penalty value may have detracted from the FOM. An example is now described.

FIG. 10 is a diagram illustrating graphically components for computing a figure of merit (FOM) from only some of the data of FIG. 4 according to embodiments. The FOM is derived by being computed on the vertical axis. The first three sets of compressions 451, 452, 453 contribute three respective components 1051, 1052, 1053, which increase the value of the FOM. The first three pauses 461, 462, 463 contribute three respective penalties 1061, 1062, 1063, which decrease the value of the FOM. Of course, penalties 1061, 1062, 1063 are shown with arrows that are inverted from arrow 563 of FIG. 5, since their value is being subtracted from the FOM. The remaining difference is value 1078 of the FOM.

Optionally, the FOM can be expressed as a fraction. The fraction can be with respect to unity, for example with "1.0" being a perfect score. Alternately, the FOM can be expressed as a percentage with respect to unity, with "100%" being the perfect score.

While FIG. 10 provides an aggregate result, its individual components may still be used for more detailed analysis. For example, a pauses table can be accumulated, listing each pause with its start time, end time, duration and penalty value. During post event review, the pauses table can be reviewed, with entries sorted by any variable, such as the penalty values from highest to lowest.

The above-mentioned devices and/or systems perform functions, processes and/or methods, as described in this document. Moreover, processes, methods and algorithms are described below. These processes, methods and algorithms are not necessarily inherently associated with any particular logic device or other apparatus. Rather, they are advantageously implemented by programs for use by a computing machine, such as a general-purpose computer, a special purpose computer, a microprocessor, etc.

Often, for the sake of convenience only, it is preferred to implement and describe a program as various interconnected distinct software modules or features, individually and collectively also known as software. This is not necessary, however, and there may be cases where modules are equivalently aggregated into a single program, even with unclear boundaries. In some instances, software is combined with hardware, in a mix called firmware.

This detailed description also includes flowcharts, display images, algorithms, and symbolic representations of program operations within at least one computer readable medium. An economy is achieved in that a single set of flowcharts is used to describe both programs, and also methods. So, while flowcharts described methods in terms of boxes, they also concurrently describe programs.

Methods are now described.

Figure 11:
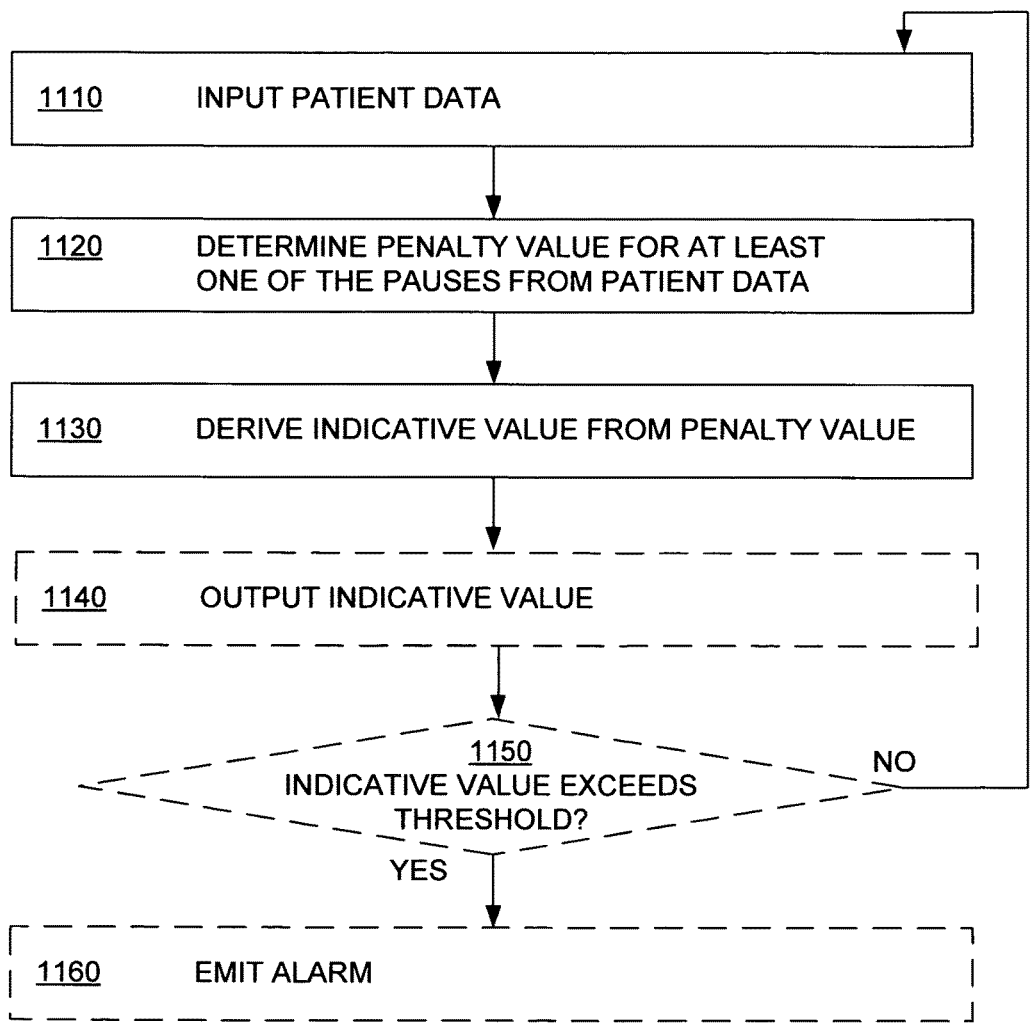
FIG. 11 is a flowchart for illustrating methods according to embodiments.

FIG. 11 shows a flowchart 1100 for describing methods according to embodiments. The methods of flowchart 1100 may also be practiced by embodiments described above, and with the ways and variations described above.

According to an operation 1110, patient data is input. The patient data may be derived from a session of administering to a patient, such as patient 182, sets of CPR chest compressions. The compressions can be separated by pauses. One or more of the pauses can be identified from the patient data, as part of operation 1110, by appropriate pattern recognition or other techniques.

According to another operation 1120, a penalty value is determined for at least a certain one of the pauses. The penalty value can be determined from at least one control factor unrelated to a constant linear dependence on a duration of the certain pause.

According to one more operation 1130, an indicative value is derived from the penalty value.

According to one more optional operation 1140, the indicative value is output. Outputting can happen by an output device, a user interface, and so on.

According to another, optional operation 1150, it is inquired whether the indicative value exceeds a threshold. If so, then according to another optional operation 1160, an alarm is emitted. If not, execution returns to operation 1110.

In some embodiments, the pauses are classified in two or more groups that can be called pause groups. The pause groups can be also called buckets and categories. The classification into pause groups can be according to different criteria. As a result, at least some of the pauses have been classified in one of these pause groups depending on how well they meet a classification criterion. Examples are now described.

Figure 12:
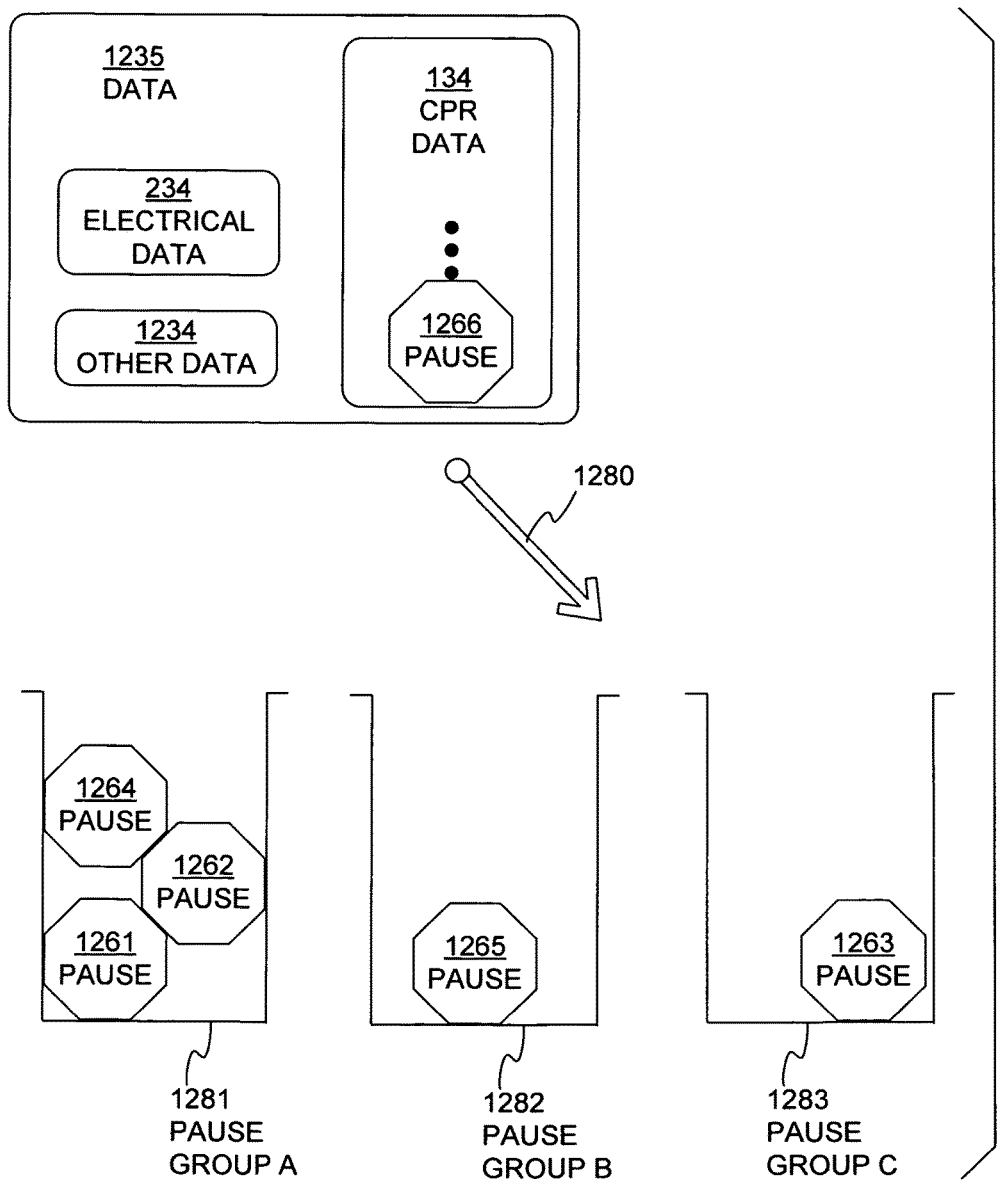
FIG. 12 is a conceptual diagram indicating classifying pauses according to embodiments.

FIG. 12 is a conceptual diagram indicating classifying pauses according to embodiments. In the example of FIG. 12, there is patient data 1235, which can include CPR data 134, electrical data 234, and other data 1234 that may have been captured about the patient, or entered by an attendant or analyst, and so on. CPR data 134 includes pauses that are identified and are represented as separate hexagonal objects, namely pauses 1261, 1262, . . . , 1266. Of course, each of pauses 1261-1266 is really a collection of data about attributes of these pauses. As will be seen later in this document, that these attributes are not merely the durations of the pauses, but may also draw from other portions of CPR data 134, electrical data 234, and other data 1234.

For classifying, in this example, there are three pause groups, namely pause group A 1281, pause group B 1282 and pause group C 1283, which are shown as buckets. The classifying is depicted by showing pauses 1261-1266 as dropping into the buckets, each directed according to arrow 1280 that could point to a different bucket, depending on how well a classification criterion is met. Pauses 1261-1265 have already been classified, while pause 1286 is about to become classified. Other pauses may follow thereafter, indicated by three dots.

In embodiments where the pauses are classified in pause groups, the indicative value can be derived for one or more of these pause groups. This way, while the pauses could exhibit disparity when compared against each other individually, they can be studied more meaningfully in summary form according to embodiments, using the groups. For example, the indicative value can be derived at least from a statistic about a number of the pauses classified in a certain pause group. The statistic can be the number of pauses in the certain pause group or bucket, or another statistic about it. The analysis can continue including different penalty values for the different pauses. Or, it can transition from the above described penalty values to statistics about groups, for example by setting the penalty value to be the same for all pauses.

As with what is written above, the indicative value can be derived having classified all the pauses in the patient data or only a number of them. Plus, an alarm can be emitted, if the indicative value exceeds a threshold.

Figure 13:
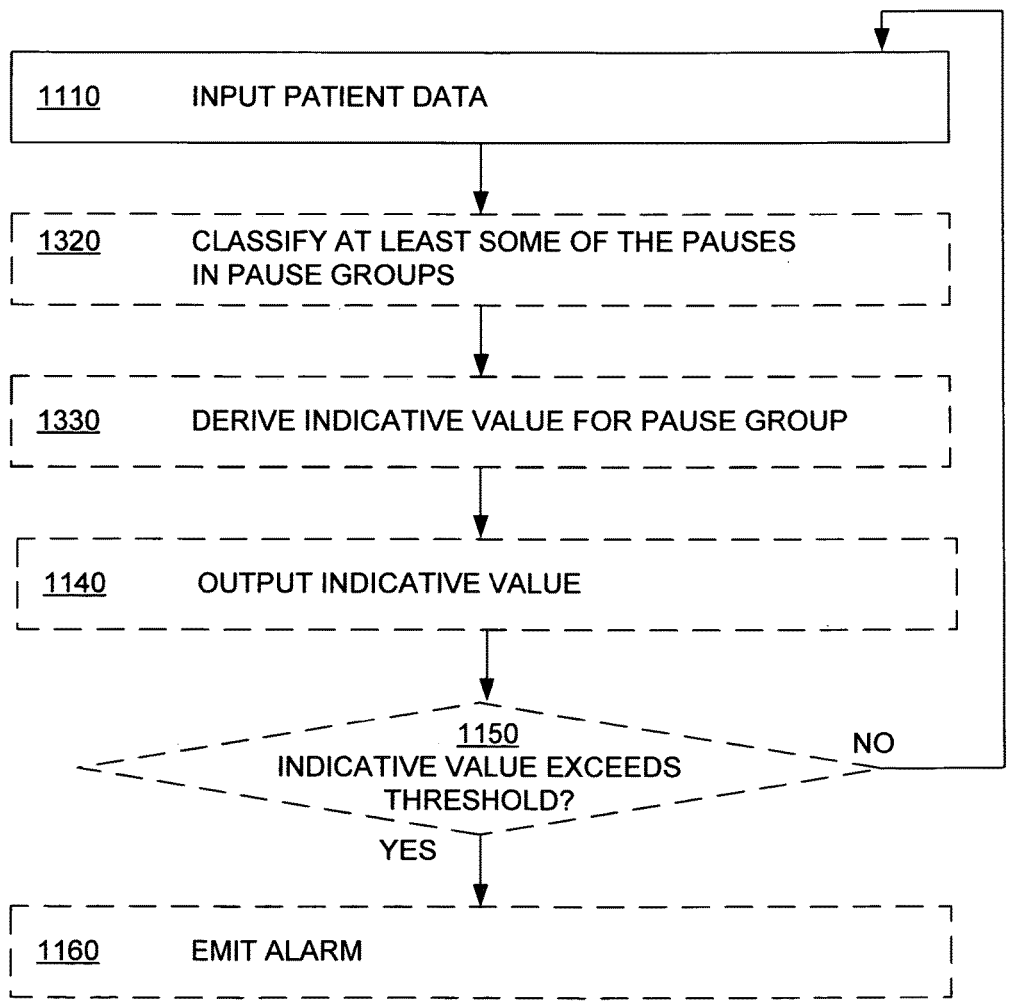
FIG. 13 is a flowchart illustrating methods according to embodiments.

FIG. 13 shows a flowchart 1300 for describing methods according to embodiments. The methods of flowchart 1300 may also be practiced by embodiments described above. Flowchart 1300 includes many of the operations of FIG. 11, and in substantially similar flow, and will not be described again.

Differently in flowchart 1300, according to an optional operation 1320, at least some of the pauses are classified in pause groups, as also mentioned elsewhere in this document. Plus, according to an optional operation 1330, the indicative value is derived for one or more of the pause groups. In such cases, the indicative value can be derived in any number of ways, such as a number of the pauses in the group, a statistic about that number, and so on.

There can be many different classification criteria according to embodiments. In many of them, the classification criterion is expressed in terms of a value, for purposes of being implemented by a processor. The value can be numerical, logical, etc. Accordingly, a pause can be classified as belonging in one, or another, of the pause groups by comparing the classification criterion with the appropriate attribute of the pause.

According to embodiments, the same set of pauses can be classified in terms of different criteria. Moreover, the same pauses can be classified in terms of the same criterion, but using different values for thresholds of the criteria. In a number of embodiments, a value for the classification criterion is input. The value could identify the type of criterion called for, the threshold that separate different pause groups, and so on.

Different types of sample classification criteria are now described. Such criteria can be advantageously related to a deleteriousness of pauses for the patient, or to causation of the pauses. Such can help evaluate the performance of a rescuer or a team. When trying to discover problems, one or more of the pause groups can be deemed not particularly deleterious, and can be ignored. (Of course, ignoring the good performance is not a fair way to evaluate a rescuer's overall performance!) Ignoring can be by ignoring a whole group, or not even defining the groups and the thresholds, so that such compressions would never even be counted.

According to embodiments, the indicative value can be displayed graphically. When there are indicative values for pause groups, they can all be displayed together, which facilitates comparison and further analysis. Examples of formats are now given, independently of the actual classification criteria being used. Additional formats can also be used, for example numerical. Plus, final reporting can include multiple formats, and include multiple categories according to embodiments. For example, a simple chest compression fraction measurement can be also computed and shown, to provide additional context and insight.

Figure 14:
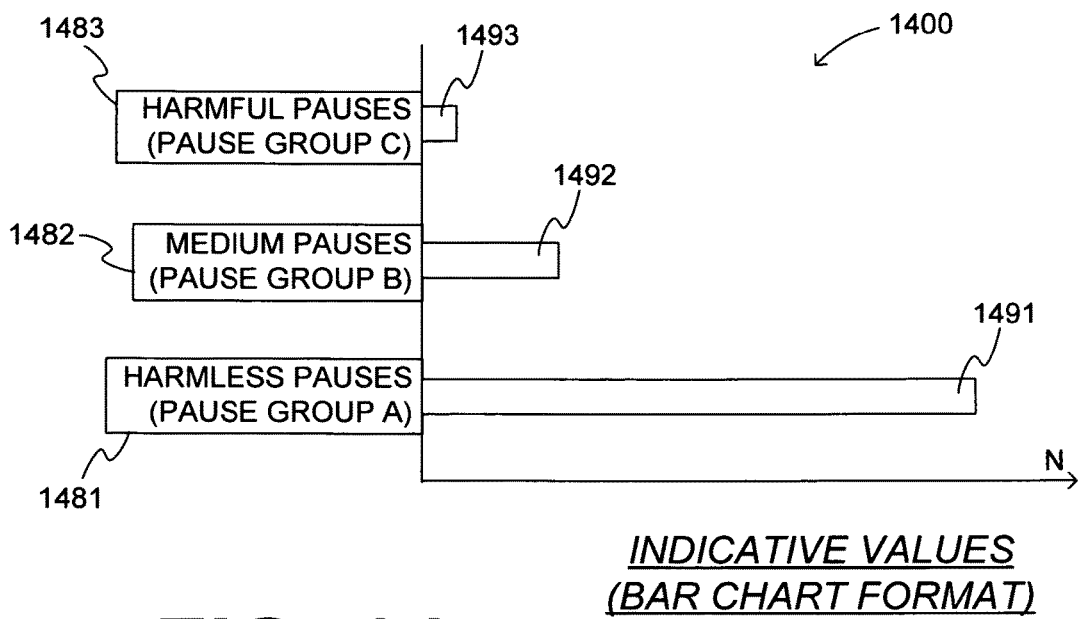
FIG. 14 is a sample diagram showing indicative values for groups in the form of a bar chart according to embodiments.

FIG. 14 is a sample diagram 1400 in the form of a bar chart. In the horizontal axis, diagram 1400 shows number of occurrences, or percentages, and so on. In the vertical axis it prints labels 1481, 1482, 1483 of pause groups. Specific labels 1481, 1482, 1483 relate to the deleteriousness of pauses, but that is not necessary. They could relate to other classification criteria for the pauses, such as causation and patient ailment. In addition, some pauses with particular durations and at particular times during the resuscitation effort may be classified as beneficial because they cause ischemic postconditioning, which has been shown in some experimental studies to improve outcome. Diagram 1400 plots bars 1491, 1492, 1493 of indicative values for respective groups 1481, 1482, 1483, as a horizontal histogram. Accordingly FIG. 14 permits a quick evaluation of performance during the session.

If it were desired to ignore the good performance, bar 1491 could be ignored. Additionally, where a value for the classification criterion is input, it can be the threshold, and thus a user will be able to configure it. Moreover, if the histogram of FIG. 14 were according to pause duration, a threshold between the two lowest pause groups can be between approximately 5 seconds and approximately 60 seconds.

Figure 15:
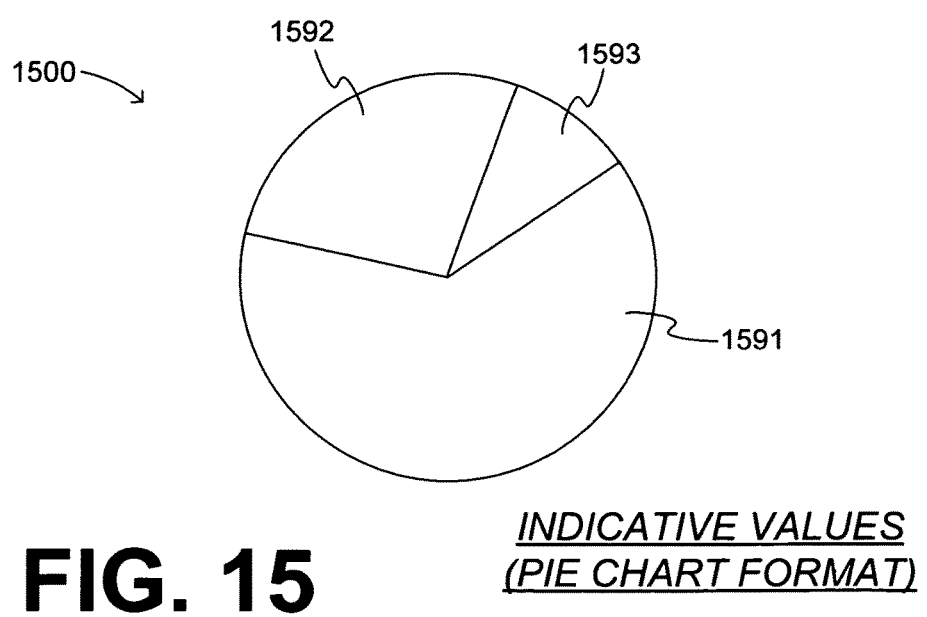
FIG. 15 is a sample diagram showing indicative values for groups in the form of a pie chart according to embodiments.

FIG. 15 is a sample diagram 1500 in the form of a pie chart, which can show number of occurrences, or percentages, and so on, relative to each other. Diagram 1500 plots pie slices 1591, 1592, 1593 of indicative values for three respective groups, which could be the same as or different from those of FIG. 14. Accordingly FIG. 15 permits a quick evaluation of performance during the session. In FIG. 15, labels could be further provided on the side of the pie chart. The pie chart of FIG. 15 would be severely distorted if a group were missing or ignored.

According to embodiments, the classification criterion can be related to a duration of the pause. Indeed, longer pauses can be more deleterious for the patient. Alternatively, some relatively long pauses may be beneficial for the patient if they are done at appropriate times for the purpose of ischemic postconditioning. Earlier in this document we also saw embodiments where the longer pauses can be accounted for by larger penalties, and in fact alarms 679 were emitted. FIGS. 14 and 15 could be labeled accordingly.

According to embodiments, the classification criterion can be related to a duration of a set of chest compressions immediately prior to the pause. If that prior set of chest compressions was not long, then circulation might not have been established for a long enough time, and then a pause can be deleterious even if not unduly long by itself. Alternatively, substantial pauses, for example 20 seconds, applied in a certain pattern during the first few minutes of the recording that includes the CPR data, might be done for ischemic postconditioning, which may be beneficial to the patient. In FIG. 4 we saw the example of set 455 that was short, and thus a subsequent pause 465 can be classified accordingly as more deleterious, while also alarm 879 was emitted. Again, such could be defined with thresholds that a user can configure. For example, the minimum threshold for the duration of the prior set of chest compressions can be set between approximately 20 seconds and approximately 120 seconds.

According to embodiments, the classification criterion can be related to a causation of the pause, i.e. what caused the pause in the CPR chest compressions. A number of possible causations include at least one of the following: initial pause, ventilation pause, peri-shock pause, intubation pause, intravenous (IV) access pause, pause for setup of a mechanical CPR device, pulse check, rhythm assessment, moving the patient, ischemic postconditioning and final pause.

Once the causation is learned, it can be displayed. There are a number of ways in which the causation can be learned. In some embodiments, a descriptive code for the causation is entered by an attendant. The attendant can be rescuer 184 in the field, or a reviewer after the fact who could be using a post-event data review tool. Such entered data can be merged with other data generated by a monitor-defibrillator, system 101, etc. In some embodiments, a descriptive code for the causation is received by a device such as system 101, a monitoring device monitoring a patient physiological parameter, movement, event data, an associated data recording device employed during the resuscitation, etc. Or receiving can be wireless, in substantially real time during a resuscitation effort. In some embodiments, a device such as the device of system 101, or a processor or software may prompt the rescuer 184 to pause chest compressions, such as for ischemic postconditioning. In such a case, the cause of the pause will be known a priori by the device, processor or software, and the descriptive code will be generated and then looked up for display by the device, processor or software itself.

Other types of sample classification criteria can be advantageously related to an ailment of the patient receiving the administered CPR chest compressions. Such may enhance understanding of physiology of patients in general and patient 182 in particular. Possible ailments include different underlying cardiac rhythms, which can be categorized against other data, such as End-Tidal Carbon Dioxide (ETCO2). There are a number of possible cardiac rhythm categories, namely a) shockable v. non-shockable, b) Ventricular Fibrillation and/or Ventricular Tachycardia v. asystole v. organized rhythm, c) Ventricular Fibrillation and/or Ventricular Tachycardia v. asystole v. organized rhythm with a heart rate less than a threshold value v. organized rhythm with a heart rate equal to or greater than a threshold value and e) organized rhythm with a heart rate equal to or greater than a threshold value, such as 40 bpm, v. all other rhythms.

There are a number of ways in which the ailment can be learned, for being displayed. In some embodiments, a descriptive code for the aliment is entered by an attendant. The attendant can be rescuer 184 in the field, or a reviewer after the fact. In some embodiments, a descriptive code for the ailment is received by a device such as system 101, a monitoring device monitoring a patient physiological parameter, movement, and so on.

In the methods described above, each operation can be performed as an affirmative step of doing, or causing to happen, what is written that can take place. Such doing or causing to happen can be by the whole system or device, or just one or more components of it. In addition, the order of operations is not constrained to what is shown, and different orders may be possible according to different embodiments. Moreover, in certain embodiments, new operations may be added, or individual operations may be modified or deleted. The added operations can be, for example, from what is mentioned while primarily describing a different system, device or method.

This description includes one or more examples, but that does not limit how the invention may be practiced. Indeed, examples or embodiments of the invention may be practiced according to what is described, or yet differently, and also in conjunction with other present or future technologies.

Reference to any prior art in this specification is not, and should not be taken as, an acknowledgement or any form of suggestion that this prior art forms parts of the common general knowledge in any country.

A person skilled in the art will be able to practice the present invention in view of this description, which is to be taken as a whole. Details have been included to provide a thorough understanding. In other instances, well-known aspects have not been described, in order to not obscure unnecessarily the present invention.

Other embodiments include combinations and sub-combinations of features described herein, including for example, embodiments that are equivalent to: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the advantages of the features incorporated in such combinations and sub-combinations.

The following claims define certain combinations and subcombinations of elements, features and steps or operations, which are regarded as novel and non-obvious. Additional claims for other such combinations and subcombinations may be presented in this or a related document.

What is claimed is:

1. A system for Cardiopulmonary Resuscitation (CPR) feedback, comprising:
   a sensor configured to detect sets of CPR chest compressions received by a patient, the sets separated by pauses;
   a base device operatively coupled with the sensor and configured to generate patient data from the detected sets;
   a user interface coupled to the base device; and a processor configured to:
receive the patient data,
identify at least some of the pauses from the patient data,
receive a classification criterion from the user interface, the classification criterion being related to the pauses in the sets of CPR chest compressions,
classify at least some of the identified pauses in one of at least two pause groups based on the classification criterion,
determine a penalty value for each pause group based on a corresponding classification, and
derive respective indicative values for each of the pause groups based on the corresponding penalty values, and
in which the user interface is configured to output the indicative values and a prompt to alter an administration of CPR chest compressions received by the patient based at least in part on the indicative values.

2. The system of claim 1, in which
the processor and the user interface are included in the base device.

3. The system of claim 1, in which
the base device further includes a defibrillation module configured to defibrillate the patient.

4. The system of claim 1, in which
the indicative values are derived at least from a statistic related to a number of the pauses classified in their respective pause groups.

5. The system of claim 1, in which
the indicative values are derived after classifying all the pauses in the patient data.

6. The system of claim 1, in which
the indicative values are derived at least once prior to classifying all the pauses in the patient data.

7. A system for Cardiopulmonary Resuscitation (CPR) feedback, comprising:
a sensor configured to detect sets of CPR chest compressions received by a patient, the sets separated by pauses;
a base device operatively coupled with the sensor and configured to generate patient data from the detected sets;
a user interface coupled to the base device; and
a processor configured to:
receive the patient data,
receive a classification criterion from the user interface, the classification criterion being related to the pauses in the sets of CPR chest compressions,
identify at least some of the pauses from the patient data,
classify at least some of the identified pauses in one of at least two pause groups based on the classification criterion,
determine a penalty value for each pause group based on a corresponding classification, wherein at least one penalty value varies non-linearly with pause duration, and
derive respective indicative values for each of the pause groups based on the corresponding penalty values, and
in which the user interface is configured to output the indicative values and a prompt to alter an administration of CPR chest compressions received by the patient, the prompt based at least in part on the indicative values.

8. The system of claim 7, in which
the base device further includes the processor, the user interface, and a defibrillation module configured to defibrillate the patient.

9. The system of claim 7, in which
the indicative values are derived at least from a statistic related to a number of the pauses classified in their respective pause groups.

10. The system of claim 7, in which
the indicative values are derived after classifying all the pauses in the patient data.

11. The system of claim 7, in which
the indicative values are derived at least once prior to classifying all the pauses in the patient data.

12. The system of claim 1, wherein the classification criterion indicates a ventilation pause.

13. The system of claim 7, wherein the classification criterion indicates an intravenous access pause.

* * * * *